United States Patent
Hoshino et al.

(10) Patent No.: US 12,091,563 B2
(45) Date of Patent: Sep. 17, 2024

(54) INKJET INK AND PRINTED ITEM

(71) Applicant: TOPPAN PRINTING CO., LTD., Tokyo (JP)

(72) Inventors: Yuichi Hoshino, Tokyo (JP); Masato Fukushiro, Tokyo (JP); Hideki Ishikawa, Tokyo (JP); Masatoshi Saito, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 215 days.

(21) Appl. No.: 17/403,581

(22) Filed: Aug. 16, 2021

(65) Prior Publication Data

US 2021/0380828 A1    Dec. 9, 2021

Related U.S. Application Data (63) Continuation of application No. PCT/JP2020/006894, filed on Feb. 20, 2020.

(30) Foreign Application Priority Data

Feb. 20, 2019    (JP) ................................ 2019-028907

(51) Int. Cl.
  *C09D 11/328*    (2014.01)
  *A61K 9/20*    (2006.01)
  *C09D 11/40*    (2014.01)

(52) U.S. Cl.
  CPC .............. *C09D 11/328* (2013.01); *A61K 9/20* (2013.01); *C09D 11/40* (2013.01)

(58) Field of Classification Search
  CPC ......... A61K 9/20; A61K 9/28; B41M 5/0023; B41M 5/0047; C09D 11/328;
  (Continued)

(56) References Cited

U.S. PATENT DOCUMENTS

| 5,273,573 | A | 12/1993 | Kappele |
| 2004/0175463 | A1* | 9/2004 | Shastry ................... A23G 3/54 426/104 |

(Continued)

FOREIGN PATENT DOCUMENTS

| CN | 105346266 A | * | 2/2016 |
| EP | 3 517 583 A1 | | 7/2019 |

(Continued)

OTHER PUBLICATIONS

Machine translation of JP 2015-218268 via EPO (Year: 2015).*
(Continued)

*Primary Examiner* — Mark Ruthkosky
*Assistant Examiner* — Rebecca L Grusby
(74) *Attorney, Agent, or Firm* — Foley & Lardner LLP (57) ABSTRACT

An inkjet ink that shows only a small amount of discoloration over time and is capable of printing with a stable color, not only when printed on a surface of a print object having a relatively low ink permeability, but also when printed on a surface of a print object having a relatively high ink permeability, and provide a printed item including a printed area printed using the inkjet ink. A gray ink according to the present embodiment is an edible inkjet ink which contains at least a first colorant which is a food dye and a second colorant which is a food dye, and the first colorant is at least one of Red No. 3, Red No. 40, Red No. 104, Red No. 105, and Red No. 106.

16 Claims, 3 Drawing Sheets

(58) Field of Classification Search
CPC ....... C09D 11/40; C09D 11/02; C09D 11/033; C09D 11/037; C09D 11/30; C09D 11/32; C09D 11/322; C09D 11/36
See application file for complete search history.

(56) References Cited

U.S. PATENT DOCUMENTS

| | | | |
|---|---|---|---|
| 2005/0003055 A1 | 1/2005 | Baydo et al. | |
| 2008/0193725 A1 | 8/2008 | De Saint-Romain | |
| 2013/0216670 A1* | 8/2013 | Willcocks | G06F 3/12 426/383 |

FOREIGN PATENT DOCUMENTS

| | | | | |
|---|---|---|---|---|
| EP | 3 778 795 A1 | 2/2021 | | |
| JP | 2006-169301 A | 6/2006 | | |
| JP | 2011236279 A | * 11/2011 | | |
| JP | 2015-218268 A | 12/2015 | | |
| JP | 2018-177810 A | 11/2018 | | |
| KR | 20030093471 A | * 12/2003 | | |
| WO | WO-9717409 A1 | * 5/1997 | ............. | C09D 11/36 |
| WO | WO-2004080191 A1 | * 9/2004 | ........... | A23G 3/0089 |
| WO | WO-2014203524 A1 | * 12/2014 | ........... | A61K 9/2072 |
| WO | WO-2017/086373 A1 | 5/2017 | | |
| WO | WO-2018116645 A1 | * 6/2018 | ................ | B41J 2/01 |
| WO | WO-2019142495 A1 | * 7/2019 | | |
| WO | WO-2019/189902 A1 | 10/2019 | | |

OTHER PUBLICATIONS

Machine translation of WO 2019/142495 via EPO (Year: 2019).*
Machine translation of WO 2018-116645 via EPO (Year: 2018).*
Machine translation of KR 2003-0093471 via EPO (Year: 2003).*
Machine translation of JP 2011-236279 via EPO (Year: 2011).*
Machine translation of WO 2014/203524 via EPO (Year: 2014).*
Machine translation of JP 2006-169301 via EPO (Year: 2006).*
Machine translation of CN 105346266 via EPO (Year: 2016).*
Partial Supplementary European Search Report dated Mar. 1, 2022 issued in corresponding European Patent Application No. 20759030.8 (14 pages).
International Searching Authority, "International Search Report," issued in connection with International Patent Application No. PCT/JP2020/006894, dated May 19, 2020.
International Searching Authority, "Written Opinion," issued in connection with International Patent Application No. PCT/JP2020/006894, dated May 19, 2020.
Extended European Search Report issued in Corresponding EP Application No. 20759030.8 dated May 11, 2022 (20 pages).

* cited by examiner

INKJET INK AND PRINTED ITEM

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2020/006894, filed on Feb. 20, 2020, which is based upon and claims the benefit of priority to Japanese Patent Application No. 2019-028907, filed on Feb. 20, 2019; the disclosures of which are incorporated herein by reference in their entireties.

BACKGROUND

The present invention relates to an inkjet ink and a printed item.

BACKGROUND ART

Some inks used for inkjet printing (hereinafter referred to simply as an "inkjet ink") are edible. A technique related to an edible inkjet ink is disclosed, for example, in PTL 1.

In some conventional inkjet inks, there are those in which a color (color tone) of printed characters, images, or the like easily changes over time, specifically, those in which discoloration over time tends to occur. When the printed color of the inkjet ink changes over time, the printed color intended by the ink designer may not be produced, and readability may be deteriorated or the color may be changed. Specifically, some conventional inkjet inks tend to show a large amount of discoloration over time when printed on a surface of a print object (printed item) having a relatively high ink permeability.

[Citation List] [Patent Literature] [PTL 1] JP 2006-169301 A

SUMMARY OF THE INVENTION

Technical Problem

The present invention has been made in view of the above described circumstances, and an object of the invention is to provide an inkjet ink which shows only a relatively small amount of discoloration over time and is capable of printing with a stable color, not only when printed on a surface of a print object having a relatively low ink permeability, but also when printed on a surface of a print object having a relatively high ink permeability, specifically, an inkjet ink exhibiting a gray color or a black color, and provide a printed item including a printed area printed using the inkjet ink.

Solution to Problem

An inkjet ink exhibiting a gray color or a black color according to an embodiment of the present invention contains at least a first colorant and a second colorant. The first colorant and the second colorant are food dyes (edible colorants) and different in color tone from each other, and the first colorant is at least one of Red No. 3, Red No. 40, Red No. 104, Red No. 105 and Red No. 106.

Advantageous Effects of Invention

The inkjet ink according to an embodiment of the present invention shows only a small amount of discoloration over time and exhibits a stable color, and maintains the printed color as gray or black, not only when printed on a surface of a print object having a relatively low ink permeability, but also when printed on a surface of a print object having a relatively high ink permeability.

DETAILED DESCRIPTION

Embodiments of the present invention of will be described below with reference to the drawings. In the following description of the drawings to be referred, components or functions identical with or similar to each other are given the same or similar reference signs, unless there is a reason not to. It should be noted that the drawings are only schematically illustrated, and thus the relationship between thickness and two-dimensional size of the components, and the thickness ratio between the layers, are not to scale. Therefore, specific thicknesses and dimensions should be understood in view of the following description. As a matter of course, dimensional relationships or ratios may be different between the drawings.

Further, the embodiments described below are merely examples of configurations for embodying the technical idea of the present invention. The technical idea of the present invention does not limit the materials, shapes, structures, arrangements, and the like of the components to those described below. The technical idea of the present invention can be modified variously within the technical scope defined by the claims. The present invention is not limited to the following embodiments within the scope not departing from the spirit of the present invention.

In any group of successive numerical value ranges described in the present specification, the upper limit value or lower limit value of one numerical value range may be replaced with the upper limit value or lower limit value of another numerical value range. In the numerical value ranges described in the present specification, the upper limit values or lower limit values of the numerical value ranges may be replaced with values shown in examples. The configuration according to a certain embodiment may be applied to other embodiments.

An inkjet ink according to an embodiment of the present invention relates to an inkjet ink that reduces discoloration over time of a printed image or the like which has been printed on a surface of, for example, a pharmaceutical tablet by an inkjet printing method. A detailed description will be given of the inkjet ink which exhibits a gray color or a black color, according to an embodiment of the present invention (hereinafter also referred to simply as a "gray ink"), and a composition of a tablet (printed item) having a printed area printed using the gray ink.

[Color Tone of Gray Inks]

The "gray color" or the "black color" exhibited by the inkjet ink according to the present embodiment is a color (color tone) defined as follows.

First, using a piezoelectric ceramic-driven drop-on-demand inkjet head having a print resolution of 600 dpi in a main scanning direction, 600 dpi in a sub-scanning direction (conveyance direction of a recording medium, such as a tablet), and having 2,656 nozzles in total, a solid image printed without overlap printing is created on a print object at an amount of 12 pL per drop.

Next, a spectrodensitometer "X-Rite 530" manufactured by X-Rite Inc. was placed over a top face of the printed solid image to measure a color tone ($L^*a^*b^*$ color system) of reflected light. The setting conditions for the above measurement are a viewing angle of 2 degrees and a D50 light source.

Among the color tones expressed in the $L^*a^*b^*$ color system measured under the above described conditions, a color (color tone) that is in the range of $L^*$ optional (0 to 100)

$a^*$ −15 to +15

$b^*$ −15 to +15 is defined as "gray" or "black" in the present embodiment.

Note that the preferred print object is, for example, a tablet having a white surface (whiteness of 70 degrees or more). The whiteness is calculated from a spectrum of reflected light measured using a spectrodensitometer "X-Rite eXact", which is manufactured by X-Rite Inc., placed over a top face of a substrate such as a tablet or a sheet of paper. The setting conditions for the above measurement comply with TAPPI-T452, which is determined by the Technical Association of the Pulp and Paper Industry (TAPPI). As the print object, instead of a tablet, a paper may also be used as long as the paper has a whiteness of 70 degrees or more.

[Composition of Gray Ink]

The gray ink according to the present embodiment is an edible inkjet ink which contains at least a first colorant and a second colorant. The first colorant and the second colorant are food dyes (edible colorants) and different in color tone from each other. The ratio of a permeation speed of the first colorant permeating into a print object to a permeation speed of the second colorant permeating into the print object (permeation speed of the first colorant/permeation speed of the second colorant) is in the range of 0.5 or more and 1.7 or less. Here, the term "permeation speed of colorant" refers to a value obtained by dividing a distance by the elapsed time (for example, 140 hours) after printing. The distance is the distance from the surface of the tablet as the print object to the lower end of an ink permeated area of the tablet (position farthest from the surface of the tablet). The distance is measured in a state in which a predetermined time (for example, 140 hours) has elapsed after printing on the tablet.

In general, a distance from the surface of a tablet as the print object to the lower end of an ink permeated area of the tablet (position farthest from the surface of the tablet) is also referred to as "permeation amount". The distance is measured when a predetermined time has elapsed after printing. Therefore, for the gray ink according to the present embodiment, the ratio of a permeation amount of the first colorant permeated into the print object to a permeation amount of the second colorant permeated into the print object (a permeation amount of the first colorant/a permeation amount of the second colorant) is set in the range of 0.5 or more and 1.7 or less.

The above described "second colorant" refers to the colorant having the highest content among the colorants contained in the gray ink according to the present embodiment.

The gray ink according to the present embodiment is, in detail, an edible inkjet ink which contains at least the first colorant and the second colorant. The first colorant and the second colorant are food dyes (edible colorants) and different in color tone from each other. The first colorant is at least one of Red No. 3 (Erythrosine, FDA Name: FD & C Red No. 3, Color Index Name: Acid Red 51, CAS Number: 16423-68-0), Red No. 40 (Allura Red AC, FDA Name: FD & C Red No. 40, Color Index Name: Food Red 17, CAS Number: 25956-17-6), Red No. 104 (Phloxine B, FDA Name: D & C Red No. 28, Color Index Name: Acid Red 92, CAS Number: 18472-87-7), Red No. 105 (Rose Bengal, Color Index Name: Acid Red 94, CAS Number: 632-69-9), and Red No. 106 (Acid Red, Color Index Name: Acid Red 52, CAS Number: 3520-42-1). The second colorant may be, for example, sodium copper chlorophyllin. With the above described composition, the gray ink according to the present embodiment shows only a small amount of discoloration over time and maintains the printed color as gray or black, not only when printed on a surface of a print object having a relatively low ink permeability, but also when printed on a surface of a print object having a relatively high ink permeability.

A description will be given below regarding this point with reference to FIGS. 1(a) to 1(c).

Figure 1A:
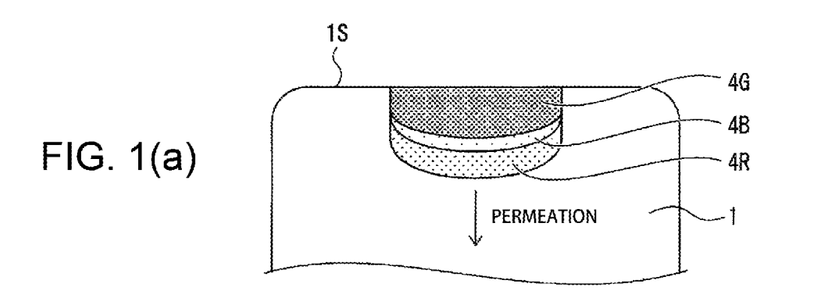
FIGS. 1(a) to 1(c) are conceptual diagrams illustrating discoloration over time of an inkjet ink.
Figure 1B:
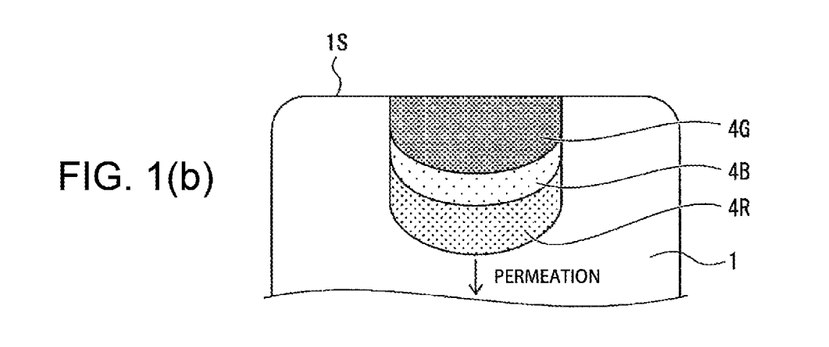
Figure 1C:
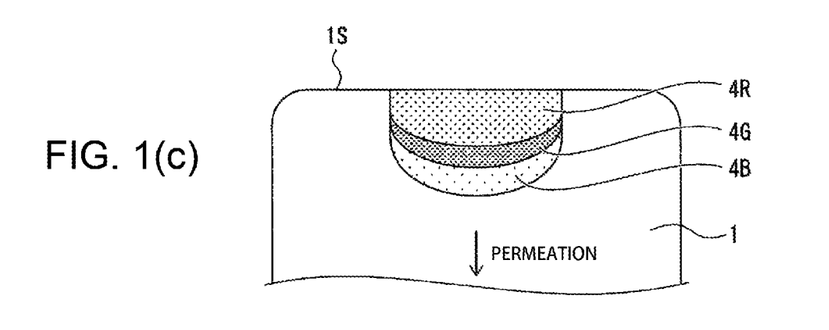

FIGS. 1(a) to 1(c) are conceptual diagrams illustrating discoloration over time of an inkjet ink. FIG. 1(a) is a cross-sectional view, in the thickness direction, of a tablet having a relatively low ink permeability in a state where a conventional gray ink is used to print on the tablet and then a predetermined time (for example, 140 hours) has elapsed. FIG. 1(b) is a cross-sectional view, in the thickness direction, of a tablet after printing using the conventional gray ink on a tablet having a relatively high ink permeability and allowing a predetermined time (for example, 140 hours) to elapse. FIG. 1(c) is a cross-sectional view, in the thickness direction, of a tablet after printing using a gray ink according to the present embodiment on a tablet having a relatively high ink permeability and allowing a predetermined time (for example, 140 hours) to elapse.

Note that, the term "a tablet having a relatively high ink permeability" refers to a tablet which has an ink permeation amount of 10 μm or more when 140 hours have elapsed after printing regardless of the type of ink. Meanwhile, the term "a tablet having a relatively low ink permeability" refers to a tablet which has an ink permeation amount of 5 μm or less when 140 hours have elapsed after printing regardless of the type of ink. The type of tablet having a relatively high ink permeability is, for example, an uncoated tablet having a coarse particle size that has a structure with a number of voids in the surface. The type of tablet having a relatively low ink permeability includes, for example, a tablet having a film coated area with few voids, specifically, a film coated tablet.

The conventional gray ink contains, for example, a food dye, Red No. 102 (New Coccine (Color Index Name: Acid Red 18, CAS Number: 2611-82-7)) as a red colorant, a food dye, Blue No. 1 (Brilliant Blue FCF (FDA Name: FD & C Blue No. 1, Color Index Name: Food Blue 2, CAS Number:

3844-45-9)) as a blue colorant, and a food dye, sodium copper chlorophyllin, as a green colorant. Other conventional gray inks contain, for example, Red No. 102, Blue No. 1, and Yellow No. 4 which is a food dye serving as a yellow colorant (Tartrazine, FDA Name: FD & C Yellow No. 5, Color Index Name: Acid Yellow 23, CAS Number: 1934-21-0). The following is an example of the conventional gray ink which contains Red No. 102, Blue No. 1, and sodium copper chlorophyllin.

The "Color Index Name" mentioned above is determined by the American Association of Textile Chemists and Colorists. The "FDA Name" mentioned above is determined by the U.S. FDA (U.S. Food and Drug Administration). Each of the available colorants (substance) is identified using CAS Number in the present embodiment but the present invention is not limited thereto. As a matter of course, for example, colorants (substances) that may be used in the present embodiment include those colorants which have the same substance names as those of the colorants (substances) described in the present embodiment but have different CAS Numbers because of being geometric isomers, stereoisomers, materials comprising isotopes, or salts thereof. If an isomer or the like is not present or an available colorant (substance) is specified (limited), the substance (compound) with CAS Number described in the present embodiment may be used.

When the conventional gray ink is used to print on a surface of a tablet having a low ink permeability, due to the low ink permeability, the permeation speeds of each of the colorants which are a red colorant 4R, a blue colorant 4B, and a green colorant 4G, become approximately the same. Therefore, as shown in FIG. 1(a), the red colorant 4R, the blue colorant 4B, and the green colorant 4G remain in the vicinity of the tablet surface 1S even after a predetermined time has elapsed after printing, and the printed color exhibits gray (black). Specifically, when the conventional gray ink is used to print on a tablet having a low ink permeability, the gray ink exhibits the same color tone as the color tone immediately after printing even after a predetermined time has elapsed after printing.

However, when the conventional gray ink is used to print on the surface of a tablet having a high ink permeability, due to the high ink permeability, a difference may occur in the permeation speeds of each of the colorants which are the red colorant 4R, the blue colorant 4B, and the green colorant 4G. This is due to the permeation speed of the red colorant 4R generally being higher than each of the permeation speeds of the blue colorant 4B and the green colorant 4G. Therefore, as shown in FIG. 1(b), the red colorant 4R permeates (migrates) into the tablet with the passage of time, while the blue colorant 4B and the green colorant 4G tend to both remain in the vicinity of the tablet surface 1S even after the passage of time. As a result, although the printed color exhibited gray (black) immediately after printing, the red color is deteriorated and the overall color of the tablet exhibits green with the passage of time. Specifically, the conventional gray ink tends to show a large amount of discoloration over time when printed on a surface of a tablet having a relatively high ink permeability. Discoloration over time tends to increase when Red No. 102 is used as the red colorant 4R.

In contrast, the gray ink according to the present embodiment contains at least a first colorant and a second colorant which has a color tone different from that of the first colorant. The ratio of the permeation speed of the first colorant permeating into a tablet to the permeation speed of the second colorant permeating into the tablet (permeation speed of the first colorant/permeation speed of the second colorant) is in the range of 0.5 or more and 1.7 or less. More specifically, the gray ink according to the present embodiment contains the first colorant and the second colorant. The first colorant contains at least one of Red No. 3, Red No. 40, Red No. 104, Red No. 105, and Red No. 106, as the red colorant 4R. The second colorant which has a different in color tone from the first colorant and contains sodium copper chlorophyllin (copper chlorophyllin Na) which is the green colorant 4G serving as the second colorant different in color tone from the first colorant. Therefore, the gray ink according to the present embodiment substantially does not contain Red No. 102 as the red colorant 4R.

The permeation speeds of each of the red colorants 4R which are Red No. 3, Red No. 40, Red No. 104, Red No. 105, and Red No. 106 used in the present embodiment are lower than the permeation speed of Red No. 102 mentioned above, and are substantially the same as the permeation speeds of other colorants such as sodium copper chlorophyllin. The term "permeation speeds are substantially the same" means that the ratio of the permeation speed of the red colorant 4R permeating into a tablet to the permeation speed of the green colorant 4G permeating into the tablet (permeation speed of the red colorant 4R/permeation speed of the green colorant 4G) is in the range of 0.5 or more and 1.7 or less.

Even when the gray ink according to the present embodiment is used to print on the surface of a tablet having a high ink permeability, each of the permeation speeds of the red colorant 4R and the green colorant 4G are approximately the same. Therefore, as shown in FIG. 1(c), after printing, the red colorant 4R and the green colorant 4G permeate into the tablet at substantially the same speed with the passage of time. Therefore, a situation can be avoided in which only specific colorants remain on the surface of the tablet, and thus the printed color exhibits substantially the same gray (black) as that immediately after printing even after a predetermined time has elapsed after printing.

FIG. 1(c) shows a case where the gray ink according to the present embodiment is used to print on a surface of a tablet having a high ink permeability. However, when the gray ink is used to print on the surface of a tablet having a low ink permeability, the red colorant 4R and the green colorant 4G remain in the vicinity of the tablet surface is, and thus the printed color exhibits substantially the same gray (black) as that immediately after printing even after a predetermined time has elapsed after printing.

The gray ink according to the present embodiment is required to contain at least one of Red No. 3, Red No. 40, Red No. 104, Red No. 105, and Red No. 106, but among them, Red No. 3 is the most preferred. Red No. 3 is less discolored over time because its permeation speed is closer to that of sodium copper chlorophyllin than other red colorants.

The content of a red colorant in the total mass of the gray ink according to the present embodiment is preferably in a range of 0.05 mass % or more and 5.0 mass % or less, and more preferably in a range of 0.1 mass % or more and 3.0 mass % or less. When the content of the red colorant is within the above described numerical value range, the color tone of gray (black) is more emphasized.

The content of sodium copper chlorophyllin as the green colorant in the total mass of the gray ink according to the present embodiment is preferably in a range of 0.4 mass % or more and 15.0 mass % or less, and more preferably in a range of 0.8 mass % or more and 12.0 mass % or less. When the content of the green colorant is within the above described numerical value range, the color tone of gray (black) is more emphasized.

The gray ink according to the present embodiment may have the content of the red colorant less than the content of the green colorant. When the content of the red colorant is less than the content of the green colorant, the color tone of gray (black) is more emphasized.

In addition to the red colorant as the first colorant and the green colorant as the second colorant, the gray ink according to the present embodiment may contain a blue colorant as a third colorant having a color tone different from those of the red colorant and the green colorant. The blue colorant serving as the third colorant may be, for example, Blue No. 1 which is a food dye. By adding a blue colorant to the red colorant and the green colorant, the color tone of gray (black) is more emphasized.

The content of the blue colorant in the total mass of the gray ink according to the present embodiment is preferably in a range of 0.05 mass % or more and 1.5 mass % or less, and more preferably in a range of 0.1 mass % or more and 1.2 mass % or less. When the content of the blue colorant is within the above described numerical value range, the color tone of gray (black) is further emphasized.

In the gray ink according to the present embodiment, the content of the blue colorant may be equal to or less than the content of the red colorant. When the content of the blue colorant is equal to or less than the content of the green colorant, the color tone of gray (black) is more emphasized.

In the gray ink according to the present embodiment, the content of the blue colorant may be equal to or less than the content of the red colorant. When the content of the blue colorant is equal to or less than the content of the green colorant, the color tone of gray (black) is more emphasized.

The total content of each of the food dyes contained in the gray ink according to the present embodiment may be in the range of 1.0 mass % or more and 15.0 mass % or less relative to the total mass of the ink. When the total content of each of the food dyes is within the above described numerical value range, the color tone of gray (black) is further emphasized. When the total content of each of the food dyes is less than 1.0 mass %, the overall printed color tends to be lighter and thus the visibility tends to decrease. When the total content of each of the food dyes is more than 15.0 mass %, the viscosity of the ink increases and the nozzles provided in the printing machine may become clogged, so the risk that printing cannot be performed increases.

(Colorant)

The colorant (color material) contained in the gray ink according to the present embodiment is not particularly limited as long as the colorant other than the above described colorant is edible. The colorant added to the gray ink according to the present embodiment is appropriately selected from, for example, conventionally known synthetic edible colorants and natural edible colorants.

Examples of the synthetic edible colorants include tar colorants, natural colorants derivatives, and natural synthetic colorants. Examples of the tar colorants include Red No. 2 (Amaranth, FDA Name: FD & C Red No. 2, Color Index Name: Acid Red 27, CAS Number: 915-67-3), Yellow No. 4 (Tartrazine, FDA Name: FD & C Yellow No. 5, Color Index Name: Acid Yellow 23, CAS Number: 1934-21-0), Yellow No. 5 (Sunset Yellow FCF, FDA Name: FD & C Yellow No. 6, Color Index Name: Food Yellow 3, CAS Number: 2783-94-0), Blue No. 2 (Indigo Carmine, FDA Name: FD & C Blue No. 2, Color Index Name: Acid Blue 74, CAS Number: 860-22-0), Red No. 2 Aluminum Lake (FD & C Red No. 2 Aluminum Lake), Red No. 3 Aluminum Lake (FD & C Red No. 3 Aluminum Lake), Red No. 40 Aluminum Lake (FD & C Red No. 40 Aluminum Lake), Yellow No. 4 Aluminum Lake (FD & C Yellow No. 5 Aluminum Lake), Yellow No. 5 Aluminum Lake (FD & C Yellow No. 6 Aluminum Lake), Blue No. 1 Aluminum Lake (FD & C Blue No. 1 Aluminum Lake), and Blue No. 2 Aluminum Lake (FD & C Blue No. 2 Aluminum Lake). The natural colorant derivatives include, for example, norbixin potassium, and the like. Examples of the natural synthetic colorants include β-carotene and riboflavin.

Examples of the natural edible colorants include anthocyanin colorants, carotenoid colorants, quinone colorants, chlorophyll colorants, flavonoid colorants, betaine colorants, Monascus colorants, and other natural colorants originating from natural products. Examples of the anthocyanin colorants include red radish colorant, red cabbage colorant, red rice colorant, elderberry colorant, cowberry colorant, gooseberry colorant, cranberry colorant, salmon berry colorant, perilla colorant, sim blueberry colorant, strawberry colorant, dark sweet cherry colorant, cherry colorant, hibiscus colorant, huckleberry colorant, grape juice colorant, grape skin colorant, black currant colorant, blackberry colorant, blueberry colorant, plum colorant, whortleberry colorant, boysenberry colorant, and mulberry colorant, purple potato colorant, purple corn colorant, Chinese purple potato colorant, raspberry colorant, red currant colorant, loganberry colorant, and other anthocyanin colorants. Examples of the carotenoid colorants include annatto colorant, gardenia yellow colorant, and other carotenoid colorants. Examples of the quinone colorants include cochineal colorant, Lithospermi radix colorant, lac colorant, and other quinone colorants. Examples of the flavonoid colorants include safflower yellow colorant, kaoliang colorant, onion colorant, and other flavonoid colorants. The betaine colorants include, for example, a beet red colorant. Examples of the Monascus colorants include Monascus red colorant and Monascus yellow colorant. Examples of other colorants originating from natural products include a turmeric colorant, a clerodendrum trichotomum colorant, a gardenia red colorant, and a spirulina blue colorant.

(Dispersion Medium)

In addition to the colorants mentioned above, the gray ink according to the present embodiment may contain a dispersion medium (solvent) to disperse (dissolve) the above described colorants. Examples of the dispersion media that may be added to the gray ink according to the present embodiment include purified water, ethanol, glycerin, propylene glycol, polyethylene glycol 300 (average molecular weight 300), 1-propanol (n-propyl alcohol), 2-propanol (isopropyl alcohol), and ethyl lactate. There is no particular limitation on the mixing ratio but the ink preferably contains any of glycerin, propylene glycol, or polyethylene glycol 300 in the range of 1 wt % or more and 30 wt % or less to prevent the ink from drying in the nozzle. If the content of the dispersion medium is less than 1 mass %, the ink may easily dry, which may possibly cause the nozzle to clog. If the content exceeds 30 mass %, an excessively long time may be taken for the printed surfaces of the pharmaceutical tablets to dry, and when these tablets are brought into contact with each other, undried ink of one tablet may adhere to another tablet and smear.

Among the above described dispersion media, by adding propylene glycol, Red No. 3 is easily dispersed as compared with other dispersion medium.

Furthermore, among the above described dispersion media, glycerin has a higher viscosity than other dispersion media and suppresses the permeation amount of the overall ink, so that the permeation speeds of each of the colorants can be substantially the same. Accordingly, with the gray ink according to the present embodiment, printing can be performed while reducing discoloration over time, even on a print object where ink permeability is relatively high and where, in general, the ink printed on the print object tends to show discoloration over time.

Although there are no limitations on the pharmaceutical tablets as a print object of the present embodiment, the effect tends to be particularly high for uncoated tablets whose surface is not coated with a film coat layer. An uncoated tablet whose surface is not coated with a film coat layer tends to be more permeable to ink than a film coated tablet whose surface is coated with a film coat layer. Therefore, the difference in permeation speeds of each of the colorants in the uncoated tablet tends to be larger than that in the film coated tablet. With the gray ink according to the present embodiment, since the difference in the permeation speeds of each of the colorants is small, a situation can be avoided in which only specific colorant components remain on the surface of the tablet, and thus discoloration over time at the printed area is reduced. Even in the film coated tablet, if the film coat layer is formed of a substance having a high ink permeability, the gray ink according to the present embodiment reduces the difference in the permeation speeds of each of the colorants, so that a situation can be avoided in which only specific colorant components remain on the surface of the tablet, and thus the change in color tone at the printed area is small.

[Printing Method]

The gray ink according to the present embodiment is not particularly limited in terms of printing method, and can be printed using an inkjet device such as a commercially available inkjet printer. Therefore, the inkjet ink according to the present embodiment has a wide range of applications and is very useful. The inkjet ink according to the present embodiment may be used for printing using a drop-on-demand inkjet device, which is actuated by piezoelectric elements (piezoelectric ceramic), or other inkjet devices.

Examples of the drop-on-demand inkjet devices include a thermal-inkjet type device ejecting an inkjet ink using water vapor pressure generated by instantaneously heating a micro-heating element to a high temperature (of 200° C. to 300° C.), an electrostatic-type device ejecting an inkjet ink by electrostatically vibrating an actuator, and an ultrasonic-type device using an ultrasonic cavitation phenomenon. A device that employs a continuous injection system (continuous type) may also be used as long as the gray ink in the present embodiment has charging performance.

[Tablet]

The gray ink according to the present embodiment may be used for printing characters or images on, for example, the surface of a tablet, using the printing methods described above. In other words, the gray ink according to the present embodiment reduces the discoloration of a printed area, or a printed image, which has been printed on, for example, the surface of a pharmaceutical tablet, using an inkjet printing method. The following description explains a composition of the tablet having a printed image printed by using the gray ink according to the present embodiment.

The tablet according to the present embodiment may be, for example, a pharmaceutical tablet. Examples of the "pharmaceutical tablet" include a film coated tablet having an outermost surface on which a water-soluble surface layer is formed, as well as an uncoated tablet (bare tablet), a sugar-coated tablet, an enteric tablet, and an orally disintegrating tablet.

Figure 2:
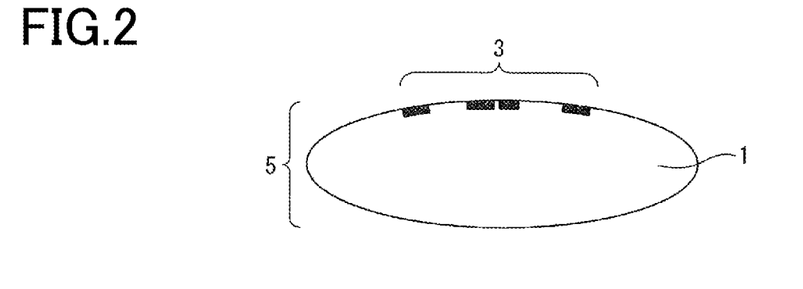
FIG. 2 is a schematic cross-sectional view illustrating an example of a tablet (uncoated tablet) according to an embodiment of the present invention.

FIG. 2 is a schematic cross-sectional view illustrating an example of a pharmaceutical tablet (uncoated tablet) having a print pattern (characters or image). FIG. 2 shows a cross section of a printed uncoated tablet 5 having a printed image 3, such as characters, printed on a top face of a tablet substrate 1.

Figure 3:
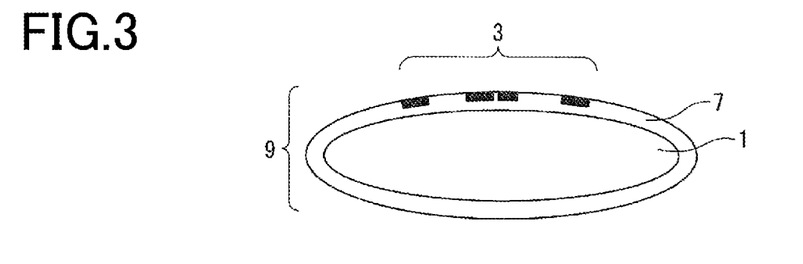
FIG. 3 is a schematic cross-sectional view illustrating an example of a tablet (film coated tablet) according to an embodiment of the present invention.

FIG. 3 is a schematic cross-sectional view illustrating an example of a pharmaceutical tablet (film coated tablet) having a print pattern (characters or image). FIG. 3 shows a cross section of a printed film coated tablet 9 in which a printed image 3, such as characters, is printed on a top face of a tablet substrate 1 having a film coat layer 7 formed on a surface thereof.

Figure 4:
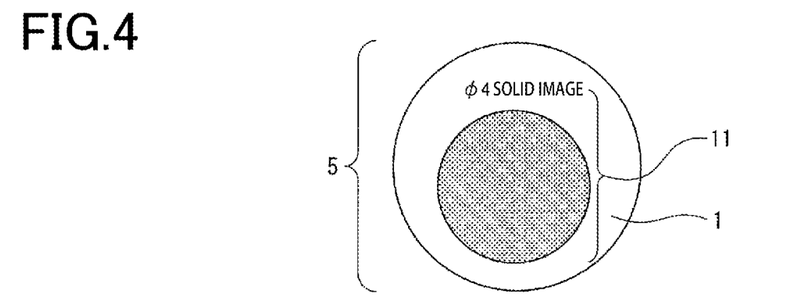
FIG. 4 is an example of a printed image provided on a tablet (uncoated tablet) according to an embodiment of the present invention.
Figure 5:
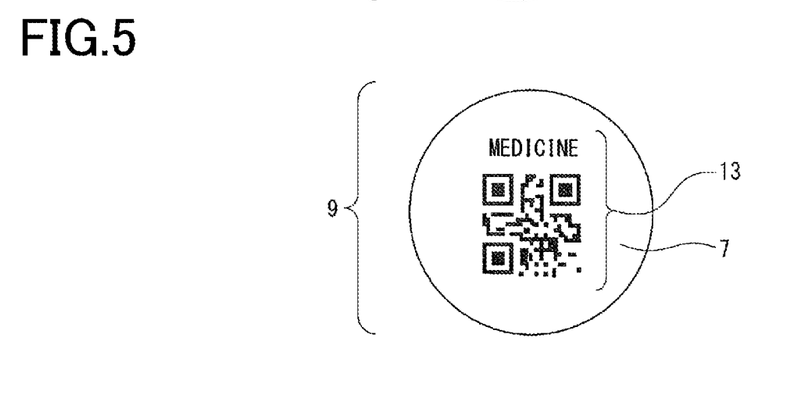
FIG. 5 is an example of a printed image provided on a tablet (film coated tablet) according to an embodiment of the present invention.

In the present embodiment, a solid image may be printed as an uncoated tablet printed image 11 as shown in FIG. 4, or a two-dimensional barcode may be printed as a film coated tablet printed image 13 as shown in FIG. 5.

There is no particular limitation on the active ingredients contained in the pharmaceutical tablet. Examples of the active ingredients include a substance effective for preventing or treating various diseases (e.g., a substance having sleep-inducing effect, an tranquilizer activity, an antibacterial activity, an antihypertensive effect, an anti-angina activity, an analgesic effect, an anti-inflammatory activity, a tranquilizing effect, a diabetes treatment activity, a diuretic effect, an anticholinergic activity, an anti-hyperacidity effect, an antiepileptic effect, an ACE inhibitory activity, a β-receptor antagonist or agonist activity, an anesthetic action, an appetite suppressant action, an antiarrhythmic effect, an antidepressant effect, an anticoagulant activity, an antidiarrheal effect, an antihistamine activity, an antimalarial effect, an antitumor activity, an immunosuppressive activity, an antiparkinsonian effect, an antipsychotic effect, an antiplatelet activity, an antihyperlipidemic effect, and the like), a substance having a scavenging effect, and a substance having a scent or a deodorant action, but are not limited thereto.

The tablet according to the present embodiment may as necessary contain a carrier that is acceptable for its application, together with an active ingredient. For example, a pharmaceutical tablet may comprise a pharmaceutically acceptable carrier. As the pharmaceutically acceptable carrier, various organic or inorganic carrier materials may be used as a material for the tablet, and an appropriate amount of excipients, lubricants, binders, disintegrating agents, thickeners or the like may be mixed thereto as appropriate. As necessary, additives, such as a preservative, an antioxidant, a coloring agent, and a sweetening agent, may also be used.

Although the present embodiment has been described taking an example of a pharmaceutical tablet as a tablet, the tablet is not limited to the tablet of the present invention. There is no particular limitation on an object to be printed on using the gray ink according to the present embodiment. For example, the gray ink may be printed on the surface of various tablets, including a feed tablet, a fertilizer tablet, a cleaning agent tablet, and a food tablet such as lemonade flavored confectionery. The gray ink of the present embodiment does not particularly limit the size of an object to be printed, but may be applied to tablets of various sizes.

[Composition of Inkjet Ink that Exhibits Colors Other than Gray (Black)]

In the present embodiment, the composition of the inkjet ink exhibiting a gray color or black color has been described, but the present invention is not limited thereto.

For example, when the inkjet ink contains at least two selected from a group of food dyes consisting of sodium copper chlorophyllin, Blue No. 1, Red No. 3, Red No. 40, Red No. 104, Red No. 105, and Red No. 106, discoloration over time is reduced. This is because the permeation speeds of each of the colorants described above are substantially the same even when printing on the surface of a print object having a relatively high ink permeability.

Since the content of the colorant in the inkjet ink described above and the solvent of the ink are the same as those in the case of the gray ink, the description thereof will be omitted here.

[Other Modifications]

In the present embodiment, the "permeation speed of colorant" is calculated by dividing a distance by the elapsed time after printing, but the present invention is not limited thereto. The distance is the distance from the surface of the tablet to the lower end of an ink permeated area of the tablet. The distance is measured in a state where a predetermined time (for example, 140 hours) has elapsed after printing on the tablet. For example, the flow rate (Rf value) of a sample, used in thin-layer chromatography, may be used. The "permeation speed of colorant" may also be calculated by dividing the flow rate (Rf value) by the time required for the colorant to migrate.

In the present embodiment, a case has been described in which a tablet having a white surface (whiteness of 70 degrees or more) is used as the print object, but the present invention is not limited thereto. The print object may be, for example, a tablet having a red surface. Even in this case, discoloration over time is reduced. Specifically, when an ink containing sodium copper chlorophyllin and Blue No. 1 is used to print on a tablet having a red surface, the printed color exhibits gray or black, and discoloration over time of the ink is small.

<Measuring Method>

The following are examples include physical properties measurement and testing of the printed tablets and inks.

(Lightfastness Test)

The test was conducted by exposing a printed tablet to solar radiation, or by using a testing machine which produces a result equivalent to that obtained from a solar radiation exposure test (Example: Xenon Weather-Ometer (Ci4000, Toyo Seiki Seisaku-sho, Ltd.)) to irradiate the printed tablet with visible light of cumulative 1.2 million lux and evaluate the color difference ΔE before and after the irradiation. The test was performed on the printed tablet.

(Moisture Resistance Test)

The test was conducted to evaluate the color difference ΔE before and after exposure of the printed tablet at 40° C. f 2° C., 75% RH f 5% RH (RH: relative humidity), in accordance with the stability test (accelerated test) for drug substances notified by the Ministry of Health, Labor and Welfare. The test was performed on the printed tablet. Exposure method: A thermostatic humidistat (Example: CSH series, manufactured by ESPEC CORP.)

(Surface Tension)

Ink was measured by platinum plate method. (Example of measuring device: DY-700, manufactured by Kyowa Interface Science Co., Ltd)

(Viscosity)

Ink was measured with a Cone-Plate Viscometer. (Example of measuring device: DVIMCP manufactured by Brookfield)

(Transmittance Absorbance)

The ink was measured with a spectrophotometer. (Example of measuring device: UV-2450 ultraviolet visible spectrophotometer, manufactured by Shimadzu Corporation.)

In the present embodiment, a description has been given of an inkjet ink having an edible property, in which the gray ink containing at least the first colorant which is a food dye and the second colorant which is a food dye and has a color tone different from that of the first colorant, in other words, an ink containing the first colorant and the second colorant in advance which is printed on a tablet or the like. However, the present invention is not limited to this. For example, even when a first inkjet ink containing at least the first colorant and a second inkjet ink containing at least the second colorant are each individually printed so as to overlap each other, the same effect as in the embodiment described above is obtained. Specifically, even when using two types of monochromatic inkjet inks individually printed so as to overlap each other, discoloration over time is small and a stable color is exhibited while the printed color is maintained as gray or black. A modification of the present embodiment will be described.

Figure 6A:
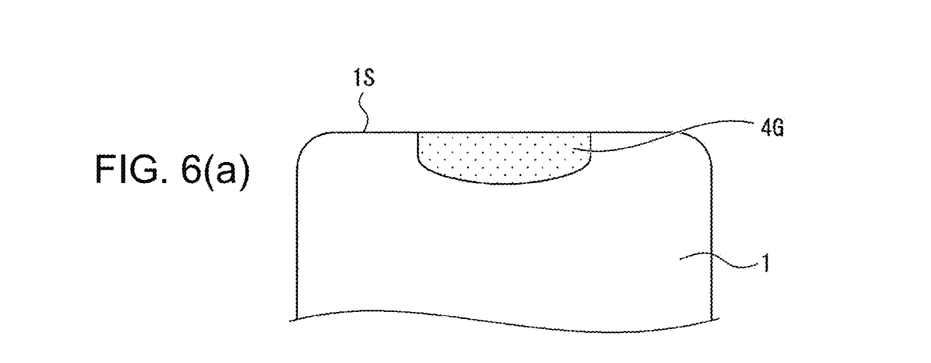
FIGS. 6(a) and 6(b) are conceptual diagrams illustrating a printing process of an inkjet ink of a modification according to an embodiment of the present invention.
Figure 6B:
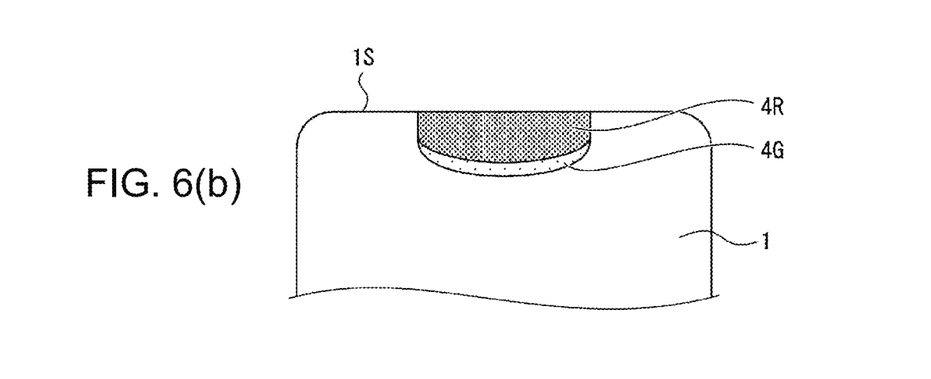

A printed item according to the modification of the present embodiment has a printed surface formed by inkjet printing, and the printed surface exhibits a gray color or a black color. The printed surface is a surface printed, in an overlapping manner, using a first inkjet ink containing at least a first colorant which is a food dye and a second inkjet ink containing at least a second colorant which is a food dye. The second colorant has a color tone different from that of the first colorant. The first colorant is at least one of Red No. 3, Red No. 40, Red No. 104, Red No. 105, and Red No. 106. For example, the printed surface provided on the printed item according to the modification of the present embodiment may be subjected to overlap printing (overprinting) by firstly printing using the second inkjet ink containing at least sodium copper chlorophyllin, as shown in FIG. 6(a), and over the second inkjet-printed ink then printing using the first inkjet ink containing at least one of Red No. 3, Red No. 40, Red No. 104, Red No. 105, and Red No. 106, as shown in FIG. 6(b).

The printed surface described above may be formed by printing using the first inkjet ink, and over the first inkjet-printed ink then printing using the second inkjet ink. There is no limitation in the order of the inkjet inks to be used for forming the printed surface.

In the printed item according to the modification of the present embodiment, the second colorant may be sodium copper chlorophyllin.

In the printed item according to the modification of the present embodiment, the first colorant may be Red No. 3.

The printed item according to the modification of the present embodiment includes a printed surface formed by printing using the first inkjet ink, the second inkjet ink, and a third inkjet ink in an overlapping manner. The third inkjet ink contains at least a third colorant which is a food dye and has a color tone different from color tones of the first colorant and the second colorant. The third colorant may be Blue No. 1. For example, the printed surface provided on a printed item according to a modification of the present embodiment may be subjected to overlap printing (overprinting) by firstly printing using a second inkjet ink containing at least sodium copper chlorophyllin, as shown in FIG. 6(a), and over the second inkjet-printed ink then printing using a first inkjet ink containing at least one of Red No. 3, Red No. 40, Red No. 104, Red No. 105, and Red No.

106, as shown in FIG. 6(b), and over the first inkjet-printed ink then printing using a third inkjet ink containing at least Blue No. 1 (not shown).

The printed surface described above may be formed by printing using the first inkjet ink, and over the first inkjet-printed ink then printing using the second inkjet ink, and over the second inkjet-printed ink then printing using the third inkjet ink. The printed surface described above may be formed by printing using the third inkjet ink, and over the third inkjet-printed ink then printing using the second inkjet ink, and over the second inkjet-printed ink then printing using the first inkjet ink. There is no limitation in the order of the inkjet inks to be used for forming the printed surface.

The printed item according to the modification of the present embodiment may have discoloration over time (ΔE) of 5 or less when 140 hours have elapsed after the formation of the printed surface.

The printed item according to the modification of the present embodiment may contain at least one of glycerin, propylene glycol, water, ethanol, and isopropyl alcohol, as a solvent contained in the ink.

The printed item according to the modification of the present embodiment may contain at least glycerin in a solvent contained in the ink.

EXAMPLES

First Example

The present invention will be described in more detail by way of examples; however, the present invention is not limited to the examples.
(Production of Inkjet Ink)

First, a printing ink was prepared. An inkjet ink contains components, specifically, a colorant (color material), an organic solvent, water (purified water), a leveling agent, and a fungicide. The first step of the preparation was to mix water with an organic solvent to produce a mixed solvent. Next, a leveling agent and a fungicide were then added to the mixed solvent to produce a transparent base liquid. Finally, a color material was added to the transparent base liquid. In this way, the ink according to the present example was prepared. The individual components will be described below.

The leveling agent is a material that adjusts a surface tension of the ink so that ink droplets ejected from the inkjet head are formed with a good shape. The surface tension of the ink is preferred to be in the range of 24 mN/m to 34 mN/m. However, considering the wettability at the surface layer of the tablet and the permeability to the inside of the tablet, it is necessary to select the smallest possible surface tension value, specifically, a surface tension value with high wettability. In the present example, the ink was prepared to have a surface tension of 24 to 28 mN/m. However, a smaller surface tension value is not always better. For example, when the surface tension value is less than 24 mN/m, droplets are not formed and thus may cause an ejection failure, such as a mist failure or a splash phenomenon (breakage of ejected ink droplets).

In the present example, ion-exchanged water was used as water (purified water) to compose the ink. As the organic solvent, at least one of glycerin, propylene glycol, and ethanol was applied.

To the aforementioned mixed solvent of water and an organic solvent, ethylparaben was added as a fungicide, followed by adding glycerin fatty acid ester (product name: "A-121E" manufactured by Taiyo Kagaku Co., Ltd.) as a leveling agent, and the mixture was stirred for about one hour to thereby obtain a transparent base liquid.

The color material was added to the transparent base liquid to obtain the inks described in Examples 1 to 22 and Comparative Example 1 and 2. The composition of each ink is shown in Table 1. The "blanks" shown in Table 1 indicate that the colorant was not added. The color tone of the inks in Examples 1 to 16, 20 to 22, and Comparative Examples 1 and 2 were gray (black). The color tone of the ink in Example 17 was bluish green, the color tone of the ink in Example 18 was red, and the color tone of the ink in Example 19 was purple.

Among color tones expressed in the L*a*b* color system measured under conditions of a viewing angle of 2 degrees and a D50 light source, the term "bluish green" refers to a color (color tone) that is in the range of L* 30 to 90
a* −80 to 0
b* −50 to 0 and to a color (color tone) that is not in the range of "gray" or "black" described above.

Among the color tones expressed in the L*a*b* color system measured under conditions of a viewing angle of 2 degrees and a D50 light source, the term "red" refers to a color (color tone) that is in the range of L* 30 to 90
a* +15 to +100
b* −10 to +15 and to a color (color tone) that is not in the range of "gray" or "black" described above.

Among the color tones expressed in the L*a*b* color system measured under conditions of a viewing angle of 2 degrees and a D50 light source, the term "purple" refers to a color (color tone) that is in the range of L* 30 to 90
a* 0 to +80
b* −50 to −10 and to a color (color tone) that is not in the range of "gray", "black", "bluish green" or "red" described above.

TABLE 1

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Color materials | (Total content of color materials) | (7.0%) | (7.0%) | (7.0%) | (1.0%) | (1.0%) | (1.0%) | (1.0%) | (1.0%) | (1.0%) | (15.0%) | (15.0%) | (7.0%) |
| | Sodium copper chlorophyllin | 6.3% | 6.0% | 6.0% | 0.8% | 0.8% | 0.8% | 0.8% | 0.8% | 0.8% | 12.0% | 12.0% | 3.0% |

TABLE 1-continued

|  |  | | | | | | | | | | | |
|---|---|---|---|---|---|---|---|---|---|---|---|---|
| | Red No. 3 | 0.7% | 0.6% | 0.6% | 0.1% | 0.2% | | | | | 1.8% | 3.0% | 4.0% |
| | Red No. 40 | | | | | | 0.2% | | | | | | |
| | Red No. 104 | | | | | | | 0.2% | | | | | |
| | Red No. 105 | | | | | | | | 0.2% | | | | |
| | Red No. 106 | | | | | | | | | 0.2% | | | |
| | Blue No. 1 | | 0.4% | 0.4% | 0.1% | | | | | | 1.2% | | |
| | Red No. 102 | | | | | | | | | | | | |
| Purified water | | 58.1% | 58.1% | 61.6% | 76.1% | 64.1% | 64.1% | 64.1% | 64.1% | 64.1% | 62.1% | 50.1% | 58.1% |
| Organic solvent | Glycerin | 20.0% | 20.0% | | 20.0% | 20.0% | 20.0% | 20.0% | 20.0% | 20.0% | 20.0% | 20.0% | 20.0% |
| | Propylene glycol | 1.5% | 1.5% | 30.0% | 1.5% | 1.5% | 1.5% | 1.5% | 1.5% | 1.5% | 1.5% | 1.5% | 1.5% |
| | Ethanol | 12% | 12% | | | 12% | 12% | 12% | 12% | 12% | | 12% | 12% |
| Glycerin fatty acid ester (A-121E) | | 0.2% | 0.2% | 0.2% | 0.2% | 0.2% | 0.2% | 0.2% | 0.2% | 0.2% | 0.2% | 0.2% | 0.2% |
| Antifungal | Ethylparaben | 1.2% | 1.2% | 1.2% | 1.2% | 1.2% | 1.2% | 1.2% | 1.2% | 1.2% | 1.2% | 1.2% | 1.2% |

| | | Examples | | | | | | | | | | Comparative Examples | |
|---|---|---|---|---|---|---|---|---|---|---|---|---|---|
| | | 13 | 14 | 15 | 16 | 17 | 18 | 19 | 20 | 21 | 22 | 1 | 2 |
| Color materials | (Total content of color materials) | (7.0%) | (7.0%) | (17.5%) | (0.5%) | (7.0%) | (7.0%) | (7.0%) | (7.0%) | (7.0%) | (7.0%) | (7.0%) | (7.0%) |
| | Sodium copper chlorophyllin | 2.8% | 6.0% | 14.0% | 0.3% | 5.0% | | | 6.0% | 6.0% | 6.3% | 3.6% | 4.0% |
| | Red No. 3 | 3.8% | 0.4% | 2.1% | 0.1% | | | | 0.6% | 0.6% | 0.7% | | |
| | Red No. 40 | | | | | | 3.5% | 2.0% | | | | | |
| | Red No. 104 | | | | | | 3.5% | 4.0% | | | | | |
| | Red No. 105 | | | | | | | | | | | | |
| | Red No. 106 | | | | | | | | | | | | |
| | Blue No. 1 | 0.4% | 0.6% | 1.4% | 0.1% | 2.0% | | 1.0% | 0.4% | 0.4% | | 0.8% | |
| | Red No. 102 | | | | | | | | | | | 2.6% | 3.0% |
| Purified water | | 58.1% | 58.1% | 47.6% | 64.6% | 58.1% | 58.1% | 58.1% | 79.6% | | | 58.1% | 70.1% |
| Organic solvent | Glycerin | 20.0% | 20.0% | 20.0% | 20.0% | 20.0% | 20.0% | 20.0% | | 79.6% | | 20.0% | 20.0% |
| | Propylene glycol | 1.5% | 1.5% | 1.5% | 1.5% | 1.5% | 1.5% | 1.5% | | | 79.6% | 1.5% | 1.5% |
| | Ethanol | 12% | 12% | 12% | 12% | 12% | 12% | 12% | 12% | 12% | 12% | 12% | |
| Glycerin fatty acid ester (A-121E) | | 0.2% | 0.2% | 0.2% | 0.2% | 0.2% | 0.2% | 0.2% | 0.2% | 0.2% | 0.2% | 0.2% | 0.2% |
| Antifungal | Ethylparaben | 1.2% | 1.2% | 1.2% | 1.2% | 1.2% | 1.2% | 1.2% | 1.2% | 1.2% | 1.2% | 1.2% | 1.2% |

Each of the inks in Examples 1 to 22 and Comparative Examples 1 and 2 was passed through membrane filters to remove solid foreign matter from the ink. In detail, each of the inks was passed once through a membrane filter (cellulose acetate film) having a pore size of 5.0 μm. Subsequently, each of the inks was passed once through a membrane filter (cellulose acetate film) having a pore size of 0.8 μm to thereby obtain the purified ink.

(Printing)

Using the purified ink, a circular solid image (4.0 mm in diameter) was printed on each of the test tablets A to D having a surface whiteness of 70 degrees or more, using an inkjet printer equipped with a bending mode piezo inkjet head. As a result, uncoated tablets and film coated tablets on which the image is printed using each of the inks of Examples 1 to 22 and Comparative Example 1 and 2 were obtained.

The components or the like of the test tablets A to D are as follows.

Test tablet A
Type of tablet: Uncoated tablet
Component: Lactose (Tablettose® 80, MEGGLE GmbH & Co. KG) 80%, cellulose 20%

Test tablet B
Type of tablet: Sustained-release uncoated tablet
Component: Lactose (Tablettose®80, MEGGLE GmbH & Co. KG) 50%, glyceryl behenate 15%, cellulose 35%

Test tablet C
Type of tablet: White film coated tablet
Substrate component: Lactose (Tablettose® 80, MEGGLE GmbH & Co. KG) 80%, cellulose 20%
Surface coating component: Hypromellose 70%, titanium oxide 20%, talc 10%

Test tablet D
Type of tablet: Clear film coated tablet
Substrate component: Lactose (Tablettose® 80, MEGGLE GmbH & Co. KG) 75%, cellulose 25%

Surface coating component: Hypromellose 100%
(Measurement of Discoloration Over Time ΔE)
<Storage Method of Printed Test Tablets>

The printed test tablets were each sealed in a light-shielding aluminum pouch, and stored in a room having a room temperature of 25° C. The printed test tablets were removed from the light-shielding aluminum pouch only when measuring discoloration over time ΔE (24, 72, 140 hours after printing), and returned back into the light-shielding aluminum pouch immediately after the measurement (within 1 minute). The reason for selecting "after 140 hours" for measuring discoloration over time ΔE in the present example will be briefly described below.

Discoloration over time occurs when a colorant permeates into a tablet or the like with time, and it was confirmed that for all the inks used in Examples 1 to 22 and Comparative Example 1 and 2 described above, the change in color (color tone) becomes saturated between 100 hours and 140 hours after printing. Therefore, the final amount of discoloration over time ΔE was measured 140 hours after printing.

<Measuring Method and Measuring Apparatus>

A circular solid image (4.0 mm in diameter) was printed on the test tablet using the inks in Examples 1 to 22 and Comparative Examples 1 and 2. A spectrodensitometer "X-Rite 530" manufactured by X-Rite Inc. was then placed over a top face of the printed solid image to measure a color tone (L*a*b* color system) of reflected light. The setting conditions for the above measurement are a viewing angle of 2 degrees and a D50 light source.

<Evaluation of Discoloration Over Time>

The evaluation of discoloration over time was determined based on the difference between the color tone immediately after printing and the color tone 140 hours after printing, specifically, the value of discoloration over time ΔE 140 hours after printing. A small value of discoloration over time ΔE indicates that the discoloration over time is small.

Excellent: Less than 3
Good: 3 or more and less than 4
Fair: 4 or more and less than 5
Poor: 5 or more When the evaluation of discoloration over time ΔE was "Excellent", "Good", or "Fair", the ink was taken to be acceptable because there was no inconvenience in use.

Hereinafter, Tables 2 to 5 shows the results of discoloration over time ΔE at each of the printed areas on a surface of the test tablets A to D on which printing is performed using each of the inks in Examples 1 to 22 and Comparative Examples 1 and 2. Note that, the term "initial color" in each table refers to a color tone immediately after printing. Numerical values listed in a column of the "initial color" are values for "L*", "a*", and "b*" measured immediately after printing.

Table 2 shows a result of the test tablet A used as a tablet.
Table 3 shows a result of the test tablet B used as a tablet.
Table 4 shows a result of the test tablet C used as a tablet.
Table 5 shows a result of the test tablet D used as a tablet.

TABLE 2

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Initial color | L* | 66 | 61 | 60 | 73 | 74 | 75 | 75 | 76 | 74 | 43 | 47 | 65 |
| | a* | −1 | 2 | 0 | −1 | 1 | 7 | 10 | 4 | 6 | 2 | 1 | 12 |
| | b* | 0 | −5 | −3 | 0 | 4 | 3 | 3 | 6 | 4 | −1 | 0 | 3 |
| Discoloration over time ΔE | 24 hours after printing | 0.9 | 0.4 | 0.6 | 1.6 | 1.1 | 2.1 | 0.8 | 0.8 | 1.4 | 0.4 | 1.0 | 1.1 |
| | 72 hours after printing | 1.4 | 1.4 | 1.9 | 2.6 | 2.5 | 3.3 | 2.1 | 2.7 | 3.2 | 1.2 | 1.6 | 1.6 |
| | 140 hours after printing | 1.7 | 2.1 | 2.9 | 3.2 | 3.6 | 4.1 | 3.9 | 4.2 | 4.6 | 1.9 | 2.0 | 1.9 |
| Determination of evaluation of discoloration over time ΔE | | Excellent | Excellent | Excellent | Good | Good | Fair | Good | Fair | Fair | Excellent | Excellent | Excellent |

| | | Examples | | | | | | | | | | Comparative Examples | |
|---|---|---|---|---|---|---|---|---|---|---|---|---|---|
| | | 13 | 14 | 15 | 16 | 17 | 18 | 19 | 20 | 21 | 22 | 1 | 2 |
| Initial color | L* | 66 | 60 | 40 | 80 | 66 | 59 | 57 | 66 | 69 | 66 | 59 | 60 |
| | a* | 10 | −2 | 1 | 2 | −28 | 48 | 21 | 0 | −5 | −1 | 2 | 3 |
| | b* | 0 | −8 | 1 | 5 | −22 | −7 | −20 | 0 | 3 | 0 | 2 | 1 |
| Discoloration over time ΔE | 24 hours after printing | 0.8 | 1.0 | 0.3 | 2.0 | 1.0 | 1.1 | 1.4 | 0.9 | 0.2 | 0.4 | 4.0 | 2.1 |
| | 72 hours after printing | 1.1 | 1.5 | 0.9 | 3.2 | 2.2 | 2.6 | 3.0 | 1.4 | 0.8 | 0.8 | 6.3 | 6.1 |
| | 140 hours after printing | 2.5 | 1.9 | 1.7 | 4.4 | 3.3 | 3.9 | 4.3 | 1.7 | 1.0 | 1.4 | 7.9 | 6.9 |

TABLE 2-continued

| | | | | | | | | | | | | |
|---|---|---|---|---|---|---|---|---|---|---|---|---|
| Determination of evaluation of discoloration over time ΔE | Excellent | Excellent | Excellent | Fair | Good | Good | Fair | Excellent | Excellent | Excellent | Poor | Poor |

TABLE 3

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Initial color | L* | 66 | 61 | 60 | 71 | 73 | 74 | 74 | 75 | 73 | 42 | 45 | 63 |
| | a* | 2 | 3 | 1 | −3 | 1 | 4 | 5 | 3 | 6 | 1 | 1 | 11 |
| | b* | 1 | −4 | −3 | 0 | 2 | 3 | 2 | 7 | 4 | 0 | 0 | 4 |
| Discoloration over time ΔE | 24 hours after printing | 0.8 | 0.7 | 2.1 | 2.2 | 1.2 | 2.3 | 1.0 | 0.8 | 1.0 | 0.5 | 1.5 | 1.1 |
| | 72 hours after printing | 2.5 | 2.3 | 3.3 | 3.5 | 2.7 | 3.7 | 2.6 | 2.7 | 3.2 | 1.8 | 2.4 | 1.7 |
| | 140 hours after printing | 3.8 | 3.6 | 4.1 | 4.4 | 3.9 | 4.6 | 4.8 | 4.2 | 4.9 | 2.7 | 3.0 | 2.1 |
| Determination of evaluation of discoloration over time ΔE | | Good | Good | Fair | Fair | Good | Fair | Fair | Fair | Fair | Excellent | Good | Excellent |

| | | Examples | | | | | | | | | | Comparative Examples | |
|---|---|---|---|---|---|---|---|---|---|---|---|---|---|
| | | 13 | 14 | 15 | 16 | 17 | 18 | 19 | 20 | 21 | 22 | 1 | 2 |
| Initial color | L* | 64 | 58 | 38 | 78 | 64 | 57 | 55 | 64 | 67 | 64 | 60 | 61 |
| | a* | 9 | −2 | 1 | 2 | −25 | 49 | 19 | 0 | −5 | −1 | 3 | 3 |
| | b* | 0 | −10 | 1 | 6 | −21 | −8 | −24 | 0 | 4 | 0 | 2 | 1 |
| Discoloration over time ΔE | 24 hours after printing | 0.8 | 1.0 | 0.3 | 2.0 | 1.0 | 1.1 | 1.4 | 0.9 | 0.2 | 0.4 | 7.1 | 5.5 |
| | 72 hours after printing | 1.2 | 1.6 | 1.0 | 3.4 | 2.4 | 2.8 | 3.2 | 1.5 | 0.9 | 0.9 | 11.4 | 8.8 |
| | 140 hours after printing | 2.8 | 2.1 | 1.9 | 4.8 | 3.6 | 4.3 | 4.7 | 1.9 | 1.1 | 1.5 | 14.2 | 11.0 |
| Determination of evaluation of discoloration over time ΔE | | Excellent | Excellent | Excellent | Fair | Good | Fair | Fair | Excellent | Excellent | Excellent | Poor | Poor |

TABLE 4

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Initial color | L* | 64 | 61 | 60 | 70 | 72 | 73 | 73 | 74 | 72 | 42 | 45 | 62 |
| | a* | 2 | 3 | 1 | −2 | 1 | 2 | 3 | 3 | 6 | 1 | 1 | 12 |
| | b* | 1 | −1 | −2 | 0 | 2 | 1 | 2 | 4 | 2 | 0 | −1 | 2 |
| Discoloration over time ΔE | 24 hours after printing | 0.2 | 0.5 | 1.2 | 1.3 | 0.6 | 1.6 | 0.7 | 0.6 | 0.6 | 0.1 | 0.5 | 0.8 |
| | 72 hours after printing | 0.7 | 0.7 | 1.9 | 2.1 | 2.0 | 2.6 | 1.8 | 2.0 | 1.9 | 0.4 | 0.8 | 1.3 |

TABLE 4-continued

|  |  |  |  |  |  |  |  |  |  |  |  |  |
|---|---|---|---|---|---|---|---|---|---|---|---|---|
| 140 hours after printing | 1.1 | 0.9 | 2.4 | 2.6 | 3.1 | 3.2 | 3.3 | 3.0 | 2.9 | 0.6 | 1.0 | 1.5 |
| Determination of evaluation of discoloration over time ΔE | Excellent | Excellent | Excellent | Excellent | Good | Good | Good | Good | Excellent | Excellent | Excellent | Excellent |

|  |  | Examples |  |  |  |  |  |  |  |  |  | Comparative Examples |  |
|---|---|---|---|---|---|---|---|---|---|---|---|---|---|
|  |  | 13 | 14 | 15 | 16 | 17 | 18 | 19 | 20 | 21 | 22 | 1 | 2 |
| Initial color | L* | 63 | 57 | 38 | 76 | 63 | 56 | 54 | 63 | 66 | 63 | 60 | 61 |
|  | a* | 9 | −3 | 1 | 2 | −32 | 50 | 20 | 1 | −6 | −1 | 2 | 2 |
|  | b* | 0 | −6 | 2 | 4 | −18 | −5 | −19 | 1 | 2 | 3 | 1 | 1 |
| Discoloration over time ΔE | 24 hours after printing | 0.6 | 0.7 | 0.2 | 1.4 | 0.6 | 0.7 | 0.8 | 0.5 | 0.1 | 0.2 | 2.6 | 1.3 |
|  | 72 hours after printing | 0.9 | 1.2 | 0.7 | 2.6 | 1.3 | 1.6 | 1.8 | 0.8 | 0.5 | 0.5 | 4.1 | 3.5 |
|  | 140 hours after printing | 2.0 | 1.5 | 1.4 | 3.5 | 2.3 | 2.7 | 3.1 | 1.2 | 0.7 | 1.0 | 5.1 | 6.3 |
| Determination of evaluation of discoloration over time ΔE |  | Excellent | Excellent | Excellent | Good | Excellent | Excellent | Good | Excellent | Excellent | Excellent | Poor | Poor |

TABLE 5

|  |  | Examples |  |  |  |  |  |  |  |  |  |  |  |
|---|---|---|---|---|---|---|---|---|---|---|---|---|---|
|  |  | 1 | 2 | 3 | 4 | 5 | 6 | 7 | 8 | 9 | 10 | 11 | 12 |
| Initial color | L* | 57 | 54 | 56 | 66 | 71 | 72 | 72 | 73 | 71 | 40 | 42 | 57 |
|  | a* | −1 | −1 | −1 | −4 | 2 | 2 | 2 | 3 | 3 | 0 | 1 | 13 |
|  | b* | 1.9 | 0.7 | 0.7 | 2 | 2 | 1 | 2 | 2 | 2 | 1 | −1 | 4 |
| Discoloration over time ΔE | 24 hours after printing | 0.4 | 0.9 | 1.5 | 1.7 | 0.8 | 2.0 | 0.8 | 0.8 | 0.7 | 0.5 | 1.5 | 1.2 |
|  | 72 hours after printing | 1.4 | 1.4 | 2.4 | 2.7 | 2.5 | 3.2 | 2.1 | 2.7 | 2.3 | 1.8 | 2.3 | 1.7 |
|  | 140 hours after printing | 2.1 | 1.7 | 3.0 | 3.4 | 3.9 | 4.0 | 3.9 | 4.2 | 3.5 | 2.7 | 2.9 | 2.1 |
| Determination of evaluation of discoloration over time ΔE |  | Excellent | Excellent | Good | Good | Good | Fair | Good | Fair | Good | Excellent | Excellent | Excellent |

|  |  | Examples |  |  |  |  |  |  |  |  |  | Comparative Examples |  |
|---|---|---|---|---|---|---|---|---|---|---|---|---|---|
|  |  | 13 | 14 | 15 | 16 | 17 | 18 | 19 | 20 | 21 | 22 | 1 | 2 |
| Initial color | L* | 57 | 52 | 35 | 70 | 57 | 51 | 50 | 57 | 60 | 57 | 57 | 60 |
|  | a* | 9 | −2 | 1 | 2 | −26 | 43 | 19 | 0 | −5 | −1 | 1 | 3 |
|  | b* | 0 | −10 | 1 | 6 | −19 | −8 | −24 | 0 | 4 | 0 | 1 | 0 |
| Discoloration over time ΔE | 24 hours after printing | 0.8 | 1.1 | 0.3 | 2.1 | 1.1 | 1.2 | 1.5 | 1.0 | 0.2 | 0.4 | 4.5 | 4.0 |
|  | 72 hours after printing | 1.5 | 1.7 | 1.2 | 2.4 | 2.0 | 2.0 | 2.4 | 2.1 | 0.9 | 0.8 | 7.2 | 6.3 |
|  | 140 hours after printing | 2.8 | 2.1 | 1.9 | 4.8 | 3.6 | 4.3 | 4.7 | 2.5 | 1.1 | 1.5 | 9.0 | 7.9 |

TABLE 5-continued

| Determination of evaluation of discoloration over time ΔE | Excellent | Excellent | Excellent | Fair | Good | Fair | Fair | Excellent | Excellent | Excellent | Poor | Poor |
|---|---|---|---|---|---|---|---|---|---|---|---|---|

(Measurement of the Permeation Amount)

In the present example, a permeation amount of each of the colorants used in Examples 1 to 22, and Comparative Example 1 and 2 is also evaluated. Hereinafter, a permeation amount of each of the colorants used in Examples 1 to 22, and Comparative Example 1 and 2 is briefly described.

First, an inkjet ink containing only one of the colorants used in Examples 1 to 22 and Comparative Example 1 and 2, specifically, a monochromatic inkjet ink, was produced. Next, the test tablets A, which were printed using the produced inkjet ink and allowed to rest for 140 hours, were each embedded in paraffin and cut out so that the cross-section could be examined using a microtome. Then, the cross section of the test tablet A was magnified 2000 times by using an optical microscope equipped with a camera, and the cross-sectional image of the test tablet A was captured.

Finally, in the captured cross-sectional image, the distance from the surface of the test tablet A to the lower end of the ink permeated area (position farthest from the surface of the test tablet) was measured. The measurement was performed on 10 samples and averaged to determine the permeation amount of each of the colorants used in Examples 1 to 22 and Comparative Examples 1 and 2.

Table 6 shows the permeation amount of each of the colorants used in Examples 1 to 22 and Comparative Example 1 and 2.

The "permeation speed" of each of the colorants used in Examples 1 to 22 and Comparative Example 1 and 2 is also calculated by dividing the distance (permeation amount) measured by the above described method by the elapsed time (140 hours) after printing.

TABLE 6

| Color material | Permeation amount after 140 hours (μm) | Permeation ratio relative to sodium copper chlorophyllin |
|---|---|---|
| Sodium copper chlorophyllin | 20 | 1.0 |
| Red No. 3 | 10 | 0.5 |
| Red No. 40 | 34 | 1.7 |
| Red No. 104 | 20 | 1.0 |
| Red No. 105 | 36 | 1.3 |
| Red No. 106 | 26 | 1.3 |
| Blue No. 1 | 32 | 1.6 |
| Red No. 102 | 56 | 2.8 |

As is apparent from the results shown in Table 6, the permeation amount (permeation speed) of Red No. 3, Red No. 40, Red No. 104, Red No. 105, Red No. 106 and Blue No. 1 are in a range of 0.5 times or more and 1.7 times or less of the permeation amount (permeation speed) of sodium copper chlorophyllin.

The permeation amount (permeation speed) of Red No. 102 is 2.8 times more than that of sodium copper chlorophyllin.

As is clear from the results shown in Tables 2 to 6, when the gray ink contains at least the first colorant and the second colorant, and the colorant having the largest content among the colorants contained in the gray ink is the second colorant, discoloration over time is reduced even when printing is performed on the surface of an uncoated tablet as a print object having a relatively high ink permeability, as in the case of printing being performed on the surface of a film coated tablet as a print object having a relatively low ink permeability, if the ratio of the permeation speed of the first colorant permeating into a tablet as a print object to the speed of the second colorant permeating into the tablet as the print object (permeation speed of the first colorant/permeation speed of the second colorant) is in the range of 0.5 or more and 1.7 or less.

Even when an ink having a color tone other than gray (black) contains at least the first colorant and the second colorant, and the colorant having the largest content among the colorants contained in the ink is the second colorant, discoloration over time is reduced even when printing is performed on the surface of an uncoated tablet as a print object having a relatively high ink permeability, as in the case of printing being performed on the surface of a film coated tablet as a print object having a relatively low ink permeability, if the ratio of a permeation speed of the first colorant permeating into a tablet as a print object to a permeation speed of the second colorant permeating into the tablet as the print object (permeation speed of the first colorant/permeation speed of the second colorant) is in a range of 0.5 or more and 1.7 or less.

If the gray ink contains at least the first colorant and the second colorant, and the first colorant is at least one of Red No. 3, Red No. 40, Red No. 104, Red No. 105, and Red No. 106, discoloration over time is reduced even when printing is performed on the surface of an uncoated tablet as a print object having a relatively high ink permeability, as in the case of printing being performed on the surface of a film coated tablet as a print object having a relatively low ink permeability.

Even when an ink has a color tone other than gray (black), if the ink contains at least the first colorant and the second colorant, and the first colorant is at least one of Red No. 3, Red No. 40, Red No. 104, Red No. 105, and Red No. 106, discoloration over time is reduced even when printing is performed on the surface of an uncoated tablet as a print object having a relatively high ink permeability, as in the case of printing being performed on the surface of a film coated tablet as a print object having a relatively low ink permeability.

Second Example

The present invention will be described in more detail by way of examples; however, the present invention is not limited to the examples.

(Production of Inkjet Ink)

First, a printing ink was prepared. An inkjet ink contains components, specifically, a colorant (color material), an organic solvent, water (purified water), a leveling agent, and a fungicide. The first step of the preparation was to mix water with an organic solvent to produce a mixed solvent. Next, a leveling agent and a fungicide were then added to the mixed solvent to produce a transparent base liquid. Finally, a color material was added to the transparent base liquid. In this way, the ink according to the present example was prepared. For each component of the organic solvent, water (purified water), the leveling agent, and the fungicide, the same components as those described in the first example were used. Therefore, in the present example, the description for each component of the organic solvent, water (purified water), the leveling agent, and the fungicide is omitted.

To the aforementioned mixed solvent of water and an organic solvent, ethylparaben was added as a fungicide, followed by adding glycerin fatty acid ester (product name: "A-121E" manufactured by Taiyo Kagaku Co., Ltd.) as a leveling agent, and the mixture was stirred for about one hour to thereby obtain a transparent base liquid.

The color material was added to the transparent base liquid to obtain the inks in Examples 23 to 28 and Comparative Example 3. Table 7 shows the composition of each of the inks. The "blanks" shown in Table 7 indicate that the colorant was not added.

TABLE 8

| | Type of ink installed in each head | | | |
|---|---|---|---|---|
| | Head A | Head B | Head C | Results |
| Example 23 | Ink A | Ink B | Empty | Good |
| Example 24 | Ink A | Ink B | Ink C | Excellent |
| Example 25 | Ink A | Ink D | Empty | Excellent |
| Example 26 | Ink A | Ink E | Empty | Good |
| Example 27 | Ink A | Ink F | Empty | Good |
| Example 28 | Ink A | Ink G | Empty | Good |
| Comparative Example 3 | Ink A | Ink B | Ink H | Poor |

(Measurement of Discoloration Over Time ΔE)
<Storage Method of Printed Test Tablets>

The printed test tablets were each sealed in a light-shielding aluminum pouch, and stored in a room having a room temperature of 25° C. The printed test tablets were

TABLE 7

| | | Inks | | | | | | | |
|---|---|---|---|---|---|---|---|---|---|
| | | A | B | C | D | E | F | G | H |
| Color material | (Total content of color materials) | (6.3%) | (0.7%) | (0.4%) | (0.7%) | (0.7%) | (0.7%) | (0.7%) | (4.5%) |
| | Sodium copper chlorophyllin | 6.3% | | | | | | | |
| | Red No. 3 | | 0.7% | | | | | | |
| | Red No. 40 | | | | 0.7% | | | | |
| | Red No. 104 | | | | | 0.7% | | | |
| | Red No. 105 | | | | | | 0.7% | | |
| | Red No. 106 | | | | | | | 0.7% | |
| | Blue No. 1 | | | 0.4% | | | | | |
| | Red No. 102 | | | | | | | | 4.5% |
| | Purified water | 58.8% | 64.4% | 64.7% | 64.4% | 64.4% | 64.4% | 64.4% | 64.4% |
| Organic solvent | Glycerin | 20.0% | 20.0% | 20.0% | 20.0% | 20.0% | 20.0% | 20.0% | 20.0% |
| | Propylene glycol | 1.5% | 1.5% | 1.5% | 1.5% | 1.5% | 1.5% | 1.5% | 1.5% |
| | Ethanol | 12% | 12% | 12% | 12% | 12% | 12% | 12% | 12% |
| | Glycerin fatty acid ester (A-121E) | 0.2% | 0.2% | 0.2% | 0.2% | 0.2% | 0.2% | 0.2% | 0.2% |
| Antifungal | Ethylparaben | 1.2% | 1.2% | 1.2% | 1.2% | 1.2% | 1.2% | 1.2% | 1.2% |

Solid foreign matter in the ink was removed by passing each of the inks described in Examples 23 to 28 and Comparative Example 3 through a membrane filter. In detail, each of the inks was passed once through a membrane filter (cellulose acetate film) having a pore size of 5.0 μm. Subsequently, each of the inks was passed once through a membrane filter (cellulose acetate film) having a pore size of 0.8 μm to thereby obtain the purified ink.

(Printing)

Using the purified ink, so-called "overprinting" was performed by using each of the inks described in Table 8 in an inkjet printer equipped with three bending mode piezo inkjet heads.

In the printer used in the present example, a head A, a head B, and a head C are arranged in parallel, and a table on which the heads are placed moves to enable overlap printing (overprinting) on the same print object.

Each head was filled with each ink in the combinations listed in Table 8, and amounts of ink ejected from each head were uniformly set to 12 pL, and printing was performed at 600 dpi. A circular solid image (4.0 mm in diameter) was printed on the test tablet A. As a result, uncoated tablets printed using each of the inks in Examples 23 to 28 and Comparative Example 3 were obtained.

The components or the like of the test tablet A are as described in the first example.

removed from the light-shielding aluminum pouch only when measuring discoloration over time ΔE (24, 72, 140 hours after printing), and returned back into the light-shielding aluminum pouch immediately after the measurement (within 1 minute).

<Evaluation of Discoloration Over Time>

The evaluation of discoloration over time was determined based on the difference between the color tone immediately after printing and the color tone 140 hours after printing, specifically, the value of discoloration over time ΔE 140 hours after printing. A small value of discoloration over time ΔE indicates that the discoloration over time is small.

Excellent: Less than 3
Good: 3 or more and less than 4
Fair: 4 or more and less than 5
Poor: 5 or more When the evaluation of discoloration over time ΔE was "Excellent", "Good", or "Fair", the ink was taken to be acceptable because there was no inconvenience in use.

As described above, even when the monochromatic ink described in the present example is overlap printed (overprinted) on the same print object, discoloration over time is reduced in the same manner as when the ink formed by mixing the monochromatic ink is used (as in the first example).

[Reference Signs List] 1: Tablet substrate; 1S: Tablet substrate surface; 3: Printed image; 4R: Red colorant; 4G: Green colorant; 4B: Blue colorant; 5: Printed uncoated tablet; 7: Film coat layer; 9: Printed film coated tablet; 11:

Uncoated tablet printed image (solid image); 13: Film coated tablet printed image (two-dimensional barcode).

What is claimed is:

1. An inkjet ink which exhibits a gray color or a black color, wherein the ink consists of:
    (a) a first colorant, which is a food dye, (b) a second colorant, which is a food dye, (c) a third colorant, which is a food dye, (d) an organic solvent, (e) 47.6 mass % to 79.6 mass % of water, (f) a leveling agent, and (g) a fungicide, wherein the second colorant has a color tone different from a color tone of the first colorant, wherein the third colorant has a color tone different from the color tone of the first colorant and the color tone of the second colorant, wherein
    the first colorant is at least one of Red No. 3, Red No. 40, Red No. 104, Red No. 105, and Red No. 106, wherein the second colorant is sodium copper chlorophyllin, and wherein the third colorant is Blue No. 1.

2. The printed item of claim 1, wherein the first colorant is the Red No. 3.

3. The printed item of claim 1, wherein a content of the first colorant is less than a content of the second colorant.

4. The printed item of claim 1, wherein a content of the third colorant is equal to or less than a content of the first colorant.

5. The printed item of claim 1, wherein a total content of the food dyes is in a range of 1 mass % or more and 15 mass % or less relative to a total content of the ink.

6. The printed item of claim 1, wherein the organic solvent comprises at least one of glycerin, propylene glycol, or ethanol.

7. The printed item of claim 1, wherein the organic solvent comprises glycerin.

8. The printed item of claim 1, wherein the printed item is a solid tablet.

9. The printed item of claim 1, wherein a content of the first colorant in the ink is in a range of 0.1 mass % or more and 3.0 mass % or less.

10. The printed item of claim 1, wherein a content of the second colorant in the ink is in a range of 0.8 mass % or more and 12.0 mass % or less.

11. The printed item of claim 1, wherein a content of the third colorant in the ink is in a range of 0.1 mass % or more and 1.2 mass % or less.

12. The printed item of claim 1, wherein a content of the first colorant in the ink is in a range of 0.1 mass % or more and 3.0 mass %, a content of the second colorant in the ink is in a range of 0.8 mass % or more and 12.0 mass % or less and a content of the third colorant in the ink is in a range of 0.1 mass % or more and 1.2 mass % or less.

13. The printed item of claim 6, wherein (i) a content of glycerin in the ink is 20 mass %, a content of propylene glycol in the ink is 1.5 mass % and a content of ethanol in the ink is 12 mass %; (ii) a content of glycerin in the ink is 20 mass %, a content of propylene glycol in the ink is 1.5 mass %; or (iii) a content of propylene glycol in the ink is 30 mass %.

14. The printed item of claim 6, wherein (i) the content of water in the ink is 58.1 mass %; a content of glycerin in the ink is 20 mass %, a content of propylene glycol in the ink is 1.5 mass % and a content of ethanol in the ink is 12 mass %; (ii) the content of water in the ink is 61.6 mass % and a content of propylene glycol in the ink is 30 mass %; (iii) the content of water in the ink is 64.1 mass %; a content of glycerin in the ink is 20 mass %, a content of propylene glycol in the ink is 1.5 mass % and a content of ethanol in the ink is 12 mass %; (iv) the content of water in the ink is 76.1 mass %; a content of glycerin in the ink is 20 mass %, and a content of propylene glycol in the ink is 1.5 mass %; (v) the content of water in the ink is 62.1%; a content of glycerin in the ink is 20%, and a content of propylene glycol in the ink is 1.5 mass %; (vi) the content of water in the ink is 50.1 mass %; a content of glycerin in the ink is 20 mass %, a content of propylene glycol in the ink is 1.5 mass % and a content of ethanol in the ink is 12 mass %; (vii) the content of water in the ink is 47.6 mass %; a content of glycerin in the ink is 20 mass %, a content of propylene glycol in the ink is 1.5 mass % and a content of ethanol in the ink is 12 mass %; (viii) the content of water in the ink is 64.6 mass %; a content of glycerin in the ink is 20%, a content of propylene glycol in the ink is 1.5 mass % and a content of ethanol in the ink is 12 mass %; or (ix) the content of water in the ink is 79.6 mass % and a content of ethanol in the ink is 12 mass %.

15. The printed item of claim 14, wherein the leveling agent is glycerin fatty acid ester and the antifungal agent is ethylparaben, wherein a content of the glycerin fatty acid ester in the ink is 0.2 mass % and a content of ethylparaben is 1.2 mass %.

16. The printed item of claim 1, consisting of (i) 6.0 mass % of sodium copper chlorophyllin, 0.6 mass % of Red No. 3, 0.4 mass % of Blue No. 1, 58.1 mass % of water, 20 mass % of glycerin, 1.5 mass % of propylene glycol, 12 mass % of ethanol, 0.2 mass % of glycerin fatty acid ester and 1.2 mass % of ethylparaben; or (ii) 6.0 mass % of sodium copper chlorophyllin, 0.6 mass % of Red No. 3, 0.4 mass % of Blue No. 1, 61.6 mass % of water, 30 mass % of propylene glycol, 0.2 mass % of glycerin fatty acid ester and 1.2 mass % of ethylparaben.

* * * * *